(12) United States Patent
Bach et al.

(10) Patent No.: US 8,487,026 B2
(45) Date of Patent: Jul. 16, 2013

(54) HOT-MELT ADHESIVE SUBSTANCE

(75) Inventors: Sebastijan Bach, Langweid (DE); Gerd Hohner, Gersthofen (DE)

(73) Assignee: Clariant Finance (BVI) Limited, Tortola (VG)

( * ) Notice: Subject to any disclaimer, the term of this patent is extended or adjusted under 35 U.S.C. 154(b) by 230 days.

(21) Appl. No.: 12/445,913

(22) PCT Filed: Oct. 6, 2007

(86) PCT No.: PCT/EP2007/008691
§ 371 (c)(1),
(2), (4) Date: Apr. 16, 2009

(87) PCT Pub. No.: WO2008/046536
PCT Pub. Date: Apr. 24, 2008

(65) Prior Publication Data
US 2010/0305531 A1    Dec. 2, 2010

(30) Foreign Application Priority Data
Oct. 18, 2006  (DE) .................. 10 2006 049 089

(51) Int. Cl.
*C08F 110/14*    (2006.01)
*C09J 193/04*    (2006.01)

(52) U.S. Cl.
USPC ........ 524/274; 524/570; 526/348.6; 526/351; 526/348.2; 526/348.3; 604/365; 523/122

(58) Field of Classification Search
USPC ............ 524/274, 570; 526/348.6, 351, 348.2, 526/348.3; 604/365; 523/122
See application file for complete search history.

(56) References Cited

U.S. PATENT DOCUMENTS

| | | | |
|---|---|---|---|
| 4,962,262 A | 10/1990 | Winter et al. | |
| 5,023,388 A | 6/1991 | Luker | |
| 5,081,322 A | 1/1992 | Winter et al. | |
| 5,639,327 A * | 6/1997 | Mody et al. ................. | 156/148 |
| 5,723,705 A | 3/1998 | Herrmann et al. | |
| 5,750,813 A | 5/1998 | Hess et al. | |
| 5,763,516 A * | 6/1998 | Godfrey .................... | 524/271 |
| 5,998,547 A | 12/1999 | Hohner | |
| 6,143,846 A | 11/2000 | Herrmann et al. | |
| 6,331,590 B1 | 12/2001 | Herrmann et al. | |
| 6,664,309 B2 | 12/2003 | Svenningsen et al. | |
| 6,747,114 B2 * | 6/2004 | Karandinos et al. ....... | 526/348.2 |
| 7,825,186 B2 | 11/2010 | Bach et al. | |
| 2002/0115744 A1 | 8/2002 | Svenningsen | |
| 2005/0054779 A1 | 3/2005 | Zhou | |
| 2006/0074171 A1 | 4/2006 | Bach et al. | |
| 2006/0222815 A1 | 10/2006 | Oles | |
| 2006/0235134 A1 | 10/2006 | Bach et al. | |
| 2007/0117894 A1 | 5/2007 | Bach et al. | |
| 2007/0117906 A1 | 5/2007 | Bach et al. | |
| 2008/0262148 A1 | 10/2008 | Bach et al. | |

FOREIGN PATENT DOCUMENTS

| | | |
|---|---|---|
| DE | 19648895 | 5/1998 |
| DE | 10323617 | 12/2004 |
| DE | 102004048536 | 4/2006 |
| EP | 0321851 | 6/1989 |
| EP | 0321852 | 6/1989 |
| EP | 0384264 | 8/1990 |
| EP | 0571882 | 12/1993 |
| EP | 0890584 | 1/1999 |
| EP | 1645608 | 4/2006 |
| WO | WO 98/23652 * | 6/1998 |
| WO | WO 01/14487 | 3/2001 |
| WO | WO 02/45763 | 6/2002 |
| WO | WO 2004/104128 | 12/2004 |

OTHER PUBLICATIONS

PCT International Search Report for PCT/EP2007/008691, mailed Jan. 17, 2008.
English Translation of International Preliminary on Patentability for PCT/EP2007/008691 mailed Jun. 18, 2009.

* cited by examiner

*Primary Examiner* — Robert D. Harlan
(74) *Attorney, Agent, or Firm* — Anthony A. Bisulca

(57) ABSTRACT

The invention relates to a hot-melt adhesive substance for sticking together fibrous materials such as matted nonwovens or woven textiles with smooth substrate surfaces, such as plastic or metal films, and for laminating said materials. Said substance is characterized in that it contains at least one polyolefin which has been produced by polymerization in the presence of metallocene as a catalyst and has a ring/ball softening point of between 50 and 165° C. and a melting viscosity, measured at a temperature of 170° C., of between 20 and 40,000 mPa-s. The hot-melt adhesive substance can also contain at least one adhesive component and is used in a quantity of between 3 and 6 g/m$^2$, preferably between 4 and 5.5 g/m$^2$, for sticking a film to a nonwoven material during the production of hygiene items such as disposable nappies, baby nappies, incontinence products, panty liners and/or sanitary towels.

24 Claims, No Drawings

HOT-MELT ADHESIVE SUBSTANCE

The invention relates to a hot melt adhesive for adhesively bonding fibrous materials such as random fiber nonwovens or woven textiles to smooth substrate surfaces such as plastic films or metal foils.

Numerous hygiene articles, in particular panty diapers and panty liners but also special wipes for cleaning and disinfection are made up, depending on their intended uses, of different, multilayer materials. Thus, panty diapers comprise an inner layer which is readily permeable to liquids, then a fibrous inner layer, preferably a nonwoven, which contains absorbent materials such as superabsorbents and finally an outer plastic film which is impermeable to water and liquids of all types. The multilayer materials have to be joined to one another sufficiently strongly for them not to delaminate or slip during their intended use and also for them to offer sufficiently good comfort when worn. Since, during use, the hygiene articles concerned are mostly in direct contact with body parts where the wearer is particularly sensitive to external irritation, they must not have any rigid or sharp holding elements which can theoretically lead to skin injuries. Furthermore, there must also be no unyielding, hard join which exerts pressure on the skin or generates friction.

These circumstances mean that the adhesives, in particular the adhesives for adhesively bonding the surface of the nonwoven to the water-impermeable film have to meet demanding requirements. Thus, the adhesive bond has to be very strong and durable even at elevated temperatures, it has to withstand considerable mechanical stresses and it must not be water-sensitive. The elasticity and flexibility of the various materials in the hygiene article and also their use properties must not be impaired by the presence of the adhesive. For toxicological and ecotoxicological reasons, solvent-free adhesives which can be applied or sprayed on in very thin layers and have a high adhesive strength even in very small amounts by weight are required. The manufacture of particularly light articles having good comfort when worn should be made possible in this way.

Hot melt adhesives containing styrene-isoprene-containing or styrene-butadiene-containing block copolymers, for example hydrogenated styrene-butadiene block copolymers obtainable under the trade name KRATON, are prior art. Styrene block copolymers as such without additional tackifiers are not sticky (do not have tack). To achieve tack and a plasticity required for the application, resins or oils are added to the styrene-containing block copolymers. These additives are permanently sticky and difficult for the user to handle. In addition, they tend to penetrate through the nonwoven, which can lead to colored spots and a less favorable optical appearance of the hygiene articles. Furthermore, relatively thick nonwoven materials are necessary when such hot melt adhesives are used, which runs counter to the consumers' desire for thin and light hygiene articles.

WO 01/14487 describes hot melt adhesives and their use as construction adhesives in the production of diapers. The hot melt adhesives contain copolymers of ethylene and $C_3$-$C_{20}$-alpha-olefins prepared in the presence of metallocene as catalyst, in particular ethylene-1-butene copolymers as are obtainable, for instance, under the trade name EXACT or ethylene-1-octene copolymers as are obtainable under the trade names AFFINITY and ENGAGE. However, the adhesive strengths of the adhesives described there are capable of improvement.

DE 102 004 048536 and DE 103 23 617 describe hot melt adhesives containing polyolefin waxes prepared using metallocene compounds as catalysts and their use. These references also disclose that such polyolefin waxes have glass transition temperatures $T_g$ of less than or equal to $-10°$ C. It was therefore an object of the present invention to develop a hot melt adhesive which is solvent-free, odorless and both toxicologically and ecotoxicologically acceptable. The hot melt adhesive sought should have a viscosity of less than 15 000 mPa·s at a temperature of 150° C. and be able to be sprayed and applied uniformly as a very thin film at temperatures in the range from 100 to 180° C., without penetrating completely through the nonwoven material. Furthermore, a hot melt adhesive which displays its full adhesive effect and develops a very good adhesive strength even at a weight per unit area of less than 6 g/m² is desired.

This object is achieved by a hot melt adhesive of the type mentioned at the outset, whose characterizing feature is that it contains at least one polyolefin which has been prepared by polymerization in the presence of metallocene as catalyst and has a ring/ball softening point in the range from 50 to 165° C. and a melt viscosity measured at a temperature of 170° C. in the range from 20 to 40 000 mPa·s.

It has surprisingly been found that the hot melt adhesive of the invention is particularly suitable as hot melt adhesive for adhesively bonding fiber materials such as nonwoven material to films and for laminating hygiene articles when it contains one or more polyolefin(s) having a glass transition temperature $T_g$ of not more than $-10°$ C. and a melt flow index MFI of greater than 30 g/10 min, measured in accordance with ISO 1133 at a temperature of 190° C. and under a load of 2.16 kg.

Furthermore, it has been found that the hot melt adhesive of the invention can also be used advantageously for the adhesive bonding of textile materials, e.g. woven fabrics.

The hot melt adhesive of the invention has outstanding properties in respect of its adhesive strength to the respective substrates even at temperatures in the range from 37 to 50° C. and it can, especially at viscosities in the range from 200 to 10 000 mPa·s at 150° C., be sprayed in a very thin layer onto surfaces. It surprisingly shows no tendency to penetrate through fibrous material such as nonwoven material or textile layers. The hot melt adhesive of the invention is not permanently sticky but becomes sticky only on processing from the melt and is therefore easy to handle for a user in the manufacture of hygiene articles of all types.

The hot melt adhesive of the invention has good internal elasticity which is retained even at low temperatures and easily withstands the repeated deformations of the nonwoven and film materials adhesively bonded by means of it. It is water-insoluble, so that undesirable detachment phenomena cannot occur in the presence of water or high atmospheric humidity.

Another advantage is the comparatively low viscosity at 100-180° C. of the hot melt adhesive of the invention, which makes particularly low processing temperatures possible. Shrinkage effects which can easily occur every now and again at high processing temperatures are thus avoided.

The hot melt adhesive of the invention preferably contains polyolefin(s) having melt viscosities measured at a temperature of 170° C. of from 50 to 30 000 mPa·s, particularly preferably from 100 to 20 000 mPa·s.

The hot melt adhesive of the invention is water- and solvent-free and also does not contain any plasticators and/or plasticizers.

Preference is also given to a hot melt adhesive containing the abovementioned polyolefins when these have a number average molar mass $M_n$ in the range from 500 to 20 000 g/mol, preferably from 800 to 10 000 g/mol, particularly preferably from 1000 to 5000 g/mol, and a weight average molar mass $M_w$ in the range from 1000 to 40 000 g/mol, preferably from 1600 to 30 000 g/mol and particularly preferably from 2000 to 20 000 g/mol. The molar mass is determined by gel permeation chromatography.

In a likewise preferred embodiment of the invention, the polyolefins present in the hot melt adhesive of the invention are homopolymers of propylene or higher 1-olefins or copolymers of olefins comprising propylene and/or higher 1-olefins and also, if appropriate, ethylene. As higher 1-olefins, preference is given to using linear or branched olefins having from 4 to 20 carbon atoms, preferably from 4 to 6 carbon atoms. These olefins can have an aromatic substituent conjugated with the olefinic double bond. Examples of possible 1-olefins are 1-butene, 1-hexene, 1-octene and 1-octadecene and also styrene. The copolymers preferably comprise from 70 to 99.9% by weight, particularly preferably from 80 to 99% by weight, of one type of olefin. Two or more of the olefins mentioned can be used for preparing the copolymers.

In a further preferred embodiment of the invention, the polyolefin present in the hot melt adhesive of the invention is a copolymer of propylene with at least one or more further monomers selected from among ethylene and linear or branched 1-olefins having from 4 to 20 carbon atoms, preferably from 4 to 10 carbon atoms, with the content of structural units derived from propylene preferably being from 70 to 99.9% by weight, particularly preferably from 80 to 99% by weight.

In a further embodiment, the polyolefin present in the hot melt adhesive is a copolymer of ethylene and at least one branched or unbranched 1-olefin having from 3 to 20 carbon atoms, with the content of structural units derived from ethylene being from 70 to 99.9% by weight.

In a particularly preferred embodiment of the invention, the polyolefin present in the hot melt adhesive is a copolymer of propylene with from 0.1 to 30% by weight, in particular from 1 to 20% by weight, of ethylene.

The hot melt adhesive of the invention preferably contains the polyolefin or polyolefins in an amount of from 2 to 100% by weight, preferably from 30 to 95% by weight, particularly preferably from 50 to 85% by weight, very particularly preferably from 70 to 80% by weight.

The hot melt adhesive of the invention additionally contains one or more tackifier(s) selected from the group of resins. Aliphatic and cycloaliphatic or aromatic hydrocarbon resins are possible. These can be prepared by polymerization of particular resin oil fractions obtained in the refining of petroleum. Such resins, which can, for example, be modified by hydrogenation or functionalization, are obtainable, for example, under the trade names Eastoflex, RegalREZ, Kristalex, Eastotac, Piccotac (Eastman Chemical Company) or Escorez (ExxonMobil Chemical Company). Further possible resins are polyterpene resins prepared by polymerization of terpenes, for example pinene, in the presence of Friedel-Crafts catalysts, likewise hydrogenated polyterpenes, copolymers and terpolymers of natural terpenes, for example styrene-terpene or α-methylstyrene-terpene copolymers. Further possibilities are natural and modified rosins, in particular resin esters, glyceryl esters of tree resins, pentaerithrityl esters of tree resins and tall oil resins and hydrogenated derivatives thereof and also phenol-modified pentaerithrityl esters of resins and phenol-modified terpene resins.

The resins mentioned are present in the hot melt adhesive of the invention either individually or in any combination in amounts, based on the total weight of the hot melt adhesive, in the range from 0 to 60% by weight, preferably from 10 to 50% by weight, particularly preferably from 15 to 30% by weight.

In a very particularly preferred embodiment of the invention, the hot melt adhesive contains one or more of the above-described polyolefins and additionally a tackifier selected from among amorphous poly-alpha-olefins, e.g. of the grades of the Vestoplast® series (Degussa) or the "Rextac" grades from Huntsman, aliphatic, cycloaliphatic or aromatic hydrocarbon resins as are obtainable, for example, under the trade name "Escorez" from ExxonMobil, also polyisobutylene obtainable, for example, under the trade name "Oppanol" from BASF. Furthermore, other polyolefins such as low-pressure polyethylenes as are available, for example, under the name "Affinity" from Dow Chemical can also be present, also high-pressure polyethylenes including those containing polar comonomers, e.g. ethylene-vinyl acetate. The total mixture of the hot melt adhesive obtained in this way has a viscosity in the range from 100 to 10 000 mPa·s at 170° C., preferably from 120 to 9000 mPa·s at 170° C., particularly preferably from 130 to 8000 mPa·s at 170° C. If appropriate, pigments, antioxidants, odor binders, antimicrobial agents or colorants and fragrances can additionally be present.

The hot melt adhesive of the invention is used in the production of various hygiene articles such as diapers, panty diapers, incontinence products, panty liners and sanitary towels, in particular for laminating fiber materials such as nonwoven materials to film.

According to the invention, the hot melt adhesive of the invention is used in amounts of from 1 to 6 g/m², preferably from 3 to 5.5 g/m², for adhesively bonding nonwoven to film.

As fibrous materials, in particular as nonwoven materials, preferably for diaper nonwovens, for total diaper construction and for incontinence products, it is possible to use natural or synthetic fiber materials composed of, for example, cotton, wool, silk, cellulose, linen, polyamide, for example Nylon or Perlon, polyester, for example polyethylene terephthalate or polypropylene terephthalate, polyvinyl chloride, polypropylene, polyethylene and also mixtures of these materials.

The films can comprise customary materials such as polyethylene terephthalate, polycarbonate, polyethylene, polypropylene, polyvinyl chloride or polystyrene, but the hot melt adhesive of the invention is also suitable for joining fibrous materials to metal surfaces composed of aluminum or iron-containing metals.

It is also possible to use woven textiles as fibrous materials. In particular, such woven textiles can be adhesively bonded to one another or to nonwoven material or films.

The invention further provides hygiene articles, preferably diapers, incontinence products, panty liners and sanitary towels, containing the hot melt adhesive of the invention.

The metallocene polyolefins present in the hot melt adhesive of the invention are prepared using metallocene compounds of the formula I as catalysts.

(I)

This formula also encompasses compounds of the formula Ia,

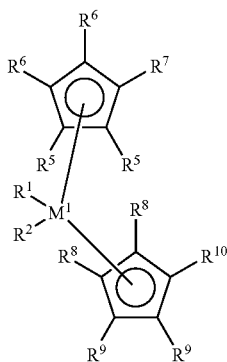

of the formula Ib,

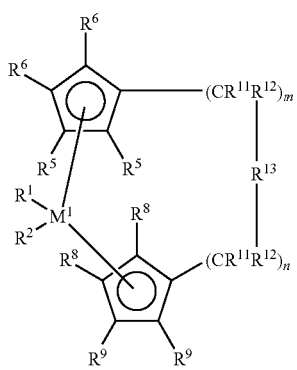

and of the formula Ic.

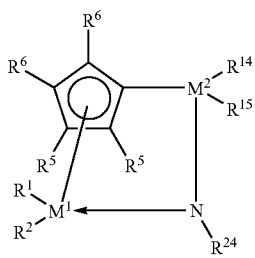

In the formulae I, Ia and Ib, $M^1$ is a metal of group IVb, Vb or VIb of the Periodic Table, for example titanium, zirconium, hafnium, vanadium, niobium, tantalum, chromium, molybdenum, tungsten, preferably titanium, zirconium and hafnium.

$R^1$ and $R^2$ are identical or different and are each a hydrogen atom, a $C_1$-$C_{10}$-, preferably $C_1$-$C_3$-alkyl group, in particular methyl, a $C_1$-$C_{10}$-, preferably $C_1$-$C_3$-alkoxy group, a $C_6$-$C_{10}$-, preferably $C_6$-$C_8$-aryl group, a $C_6$-$C_{10}$-, preferably $C_6$-$C_8$-aryloxy group, a $C_2$-$C_{10}$-, preferably $C_2$-$C_4$-alkenyl group, a $C_7$-$C_{40}$-, preferably $C_7$-$C_{10}$-arylalkyl group, a $C_7$-$C_{40}$-, preferably $C_7$-$C_{12}$-alkylaryl group, a $C_8$-$C_{40}$-, preferably $C_8$-$C_{12}$-arylalkenyl group or a halogen, preferably chlorine atom.

$R^3$ and $R^4$ are identical or different and are each a monocyclic or polycyclic hydrocarbon radical which can form a sandwich structure with the central atom $M^1$. $R^3$ and $R^4$ are preferably cyclopentadienyl, indenyl, tetrahydroindenyl, benzoindenyl or fluorenyl, with the basic molecules also being able to bear additional substituents or be bridged to one another. In addition, one of the radicals $R^3$ and $R^4$ can be a substituted nitrogen atom, where $R^{24}$ has the meaning of $R^{17}$ and is preferably methyl, tert-butyl or cyclohexyl.

$R^5$, $R^6$, $R^7$, $R^8$, $R^9$ and $R^{10}$ are identical or different and are each a hydrogen atom, a halogen atom, preferably a fluorine, chlorine or bromine atom, a $C_1$-$C_{10}$-, preferably $C_1$-$C_4$-alkyl group, a $C_6$-$C_{10}$-, preferably $C_6$-$C_8$-aryl group, a $C_1$-$C_{10}$-, preferably $C_1$-$C_3$-alkoxy group, a —$NR^{16}{}_2$, —$SR^{16}$, —$OSiR^{16}{}_3$, —$SiR^{16}{}_3$ or —$PR^{16}{}_2$ radical, where $R^{16}$ is a $C_1$-$C_{10}$-, preferably $C_1$-$C_3$-alkyl group or a $C_6$-$C_{10}$-, preferably $C_6$-$C_8$-aryl group or in the case of Si- or P-containing radicals can also be a halogen atom, preferably a chlorine atom, or two adjacent radicals $R^5$, $R^6$, $R^7$, $R^8$, $R^9$ or $R^{10}$ together with the carbon atoms connecting them form a ring. Particularly preferred ligands are the substituted compounds of the basic molecules cyclopentadienyl, indenyl, tetrahydroindenyl, benzoindenyl or fluorenyl.

$R^{13}$ is

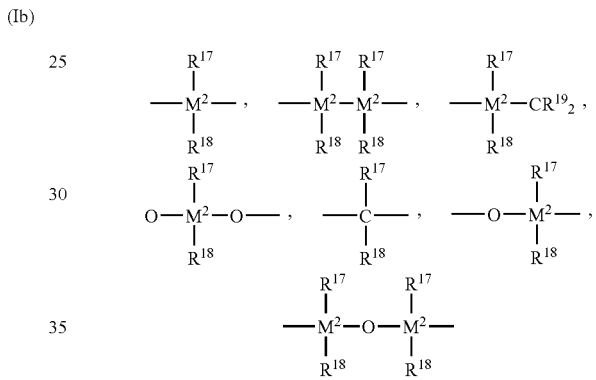

=$BR^{17}$, =$AlR^{17}$, —Ge—, —Sn—, —O—, —S—, =SO, =$SO_2$, =$NR^{17}$, =CO, =$PR^{17}$ or =$P(O)R^{17}$, where $R^{17}$, $R^{18}$ and $R^{19}$ are identical or different and are each a hydrogen atom, a halogen atom, preferably a fluorine, chlorine or bromine atom, a $C_1$-$C_{30}$-, preferably $C_1$-$C_4$-alkyl group, in particular a methyl group, a $C_1$-$C_{10}$-fluoroalkyl, preferably $CF_3$ group, a $C_6$-$C_{10}$-fluoroaryl, preferably a pentafluorophenyl group, a $C_6$-$C_{10}$-, preferably $C_6$-$C_8$-aryl group, a $C_1$-$C_{10}$-, preferably $C_1$-$C_4$-alkoxy group, in particular a methoxy group, a $C_2$-$C_{10}$-, preferably $C_2$-$C_4$-alkenyl group, a $C_7$-$C_{40}$-, preferably $C_7$-$C_{10}$-aralkyl group, a $C_8$-$C_{40}$-, preferably $C_8$-$C_{12}$-arylalkenyl group or a $C_7$-$C_{40}$-, preferably $C_7$-$C_{12}$-alkylaryl group, or $R^{17}$ and $R^{18}$ or $R^{17}$ and $R^{19}$ in each case together with the atoms connecting them form a ring.

$M^2$ is silicon, germanium or tin, preferably silicon or germanium. $R^{13}$ is preferably =$CR^{17}R^{18}$, =$SiR^{17}R^{18}$, =$GeR^{17}R^{18}$, —O—, —S—, =SO, =$PR^{17}$ or =$P(O)R^{17}$.

$R^{11}$ and $R^{12}$ are identical or different and have the meaning given for $R^{17}$. m and n are identical or different and are each zero, 1 or 2, preferably zero or 1, where m plus n is zero, 1 or 2, preferably zero or 1.

$R^{14}$ and $R^{15}$ have the meanings of $R^{17}$ and $R^{18}$.

Specific examples of suitable metallocenes are:
bis(1,2,3-trimethylcyclopentadienyl)zirconium dichloride,
bis(1,2,4-trimethylcyclopentadienyl)zirconium dichloride,
bis(1,2-dimethylcyclopentadienyl)zirconium dichloride,
bis(1,3-dimethylcyclopentadienyl)zirconium dichloride, bis(1-methylindenyl)zirconium dichloride,
bis(1-n-butyl-3-methylcyclopentadienyl)zirconium dichloride,
bis(2-methyl-4,6-di-i-propylindenyl)zirconium dichloride,
bis(2-methylindenyl)zirconium dichloride,
bis(4-methylindenyl)zirconium dichloride,
bis(5-methylindenyl)zirconium dichloride,
bis(alkylcyclopentadienyl)zirconium dichloride,
bis(alkylindenyl)zirconium dichloride,
bis(cyclopentadienyl)zirconium dichloride,
bis(indenyl)zirconium dichloride,
bis(methylcyclopentadienyl)zirconium dichloride,
bis(n-butylcyclopentadienyl)zirconium dichloride,
bis(octadecylcyclopentadienyl)zirconium dichloride,
bis(pentamethylcyclopentadienyl)zirconium dichloride,
bis(trimethylsilylcyclopentadienyl)zirconium dichloride,
biscyclopentadienyldibenzylzirconium,
biscyclopentadienyldimethylzirconium,
bistetrahydroindenylzirconium dichloride,
dimethylsilyl-9-fluorenylcyclopentadienylzirconium dichloride,
dimethylsilylbis-1-(2,3,5-trimethylcyclopentadienyl)zirconium dichloride,
dimethylsilylbis-1-(2,4-dimethylcyclopentadienyl)zirconium dichloride,
dimethylsilylbis-1-(2-methyl-4,5-benzoindenyl)zirconium dichloride,
dimethylsilylbis-1-(2-methyl-4-ethylindenyl)zirconium dichloride,
dimethylsilylbis-1-(2-methyl-4-i-propylindenyl)zirconium dichloride,
dimethylsilylbis-1-(2-methyl-4-phenylindenyl)zirconium dichloride,
dimethylsilylbis-1-(2-methylindenyl)zirconium dichloride,
dimethylsilylbis-1-(2-methyltetrahydroindenyl)zirconium dichloride,
dimethylsilylbis-1-indenylzirconium dichloride,
dimethylsilylbis-1-indenyldimethylzirconium,
dimethylsilylbis-1-tetrahydroindenylzirconium dichloride,
diphenylmethylene-9-fluorenylcyclopentadienylzirconium dichloride,
diphenylsilylbis-1-indenylzirconium dichloride,
ethylenebis-1-(2-methyl-4,5-benzoindenyl)zirconium dichloride,
ethylenebis-1-(2-methyl-4-phenylindenyl)zirconium dichloride,
ethylenebis-1-(2-methyltetrahydroindenyl)zirconium dichloride,
ethylenebis-1-(4,7-dimethylindenyl)zirconium dichloride,
ethylenebis-1-indenylzirconium dichloride,
ethylenebis-1-tetrahydroindenylzirconium dichloride,
indenylcyclopentadienylzirconium dichloride,
isopropylidene(1-indenyl)(cyclopentadienyl)zirconium dichloride,
isopropylidene(9-fluorenyl)(cyclopentadienyl)zirconium dichloride,
phenylmethylsilylbis-1-(2-methylindenyl)zirconium dichloride,
and also the alkyl or aryl derivatives of each of these metallocene dichlorides.

To activate the single-site catalyst systems, use is made of suitable cocatalysts. Suitable cocatalysts for metallocenes of the formula I are organoaluminum compounds, in particular aluminoxanes or else aluminum-free systems such as $R^{20}{}_x NH_{4-x} BR^{21}{}_4$, $R^{20}{}_x PH_{4-x} BR^{21}{}_4$, $R^{20}{}_3 CBR^{21}{}_4$ or $BR^{21}{}_3$. In these formulae, x is from 1 to 4, the radicals $R^{20}$ are identical or different, preferably identical, and are each $C_1$-$C_{10}$-alkyl or $C_6$-$C_{18}$-aryl or two radicals $R^{20}$ together with the atom connecting them form a ring and the radicals $R^{21}$ are identical or different, preferably identical, and are each $C_6$-$C_{18}$-aryl which may be substituted by alkyl, haloalkyl or fluorine. In particular, $R^{20}$ is ethyl, propyl, butyl or phenyl and $R^{21}$ is phenyl, pentafluorophenyl, 3,5-bistrifluoromethylphenyl, mesityl, xylyl or tolyl.

In addition, a third component is frequently necessary to maintain protection against polar catalyst poisons. Organoaluminum compounds such as triethylaluminum, tributylaluminum and others and also mixtures of these are suitable for this purpose.

Depending on the process, it is also possible to use supported single-site catalysts. Preference is given to catalyst systems in which the residual contents of support material and cocatalyst do not exceed a concentration of 100 ppm in the product.

Processes for preparing such polyolefins are described in the prior art, for example EP-A-0 321 851, EP-A-0 321 852, EP-A-0 384 264, EP-A-0 571 882 and EP-A-0 890 584.

EXAMPLES

The following examples illustrate the invention but do not restrict it to the specific embodiments described.

Percentages are, unless indicated otherwise, by weight.

The melt viscosities were determined in accordance with DIN 53019 using a rotational viscosimeter, the dropping points were determined in accordance with ASTM D3954, the ring/ball softening points were determined in accordance with ASTM D3104. The weight average molar mass $M_w$ and the number average molar mass $M_n$ were determined by gel permeation chromatography at a temperature of 135° C. in 1,2-dichloro-benzene.

The polyolefins 1 to 4 which were used according to the invention and are shown in Table 1 were prepared by methods of the prior art as described in EP 0 384 264 or EP 0 571 882.

TABLE 1

| | Polyolefins used | | | |
|---|---|---|---|---|
| | Polyolefin 1 | Polyolefin 2 | Polyolefin 3 | Polyolefin 4 |
| Preparation according to | EP 0 384 264 general method Ex. 1-16[1)] | EP 0 384 264 general method Ex. 1-16[2)] | EP 0 571 882 Ex. 3 | EP 0 384 264 general method Ex. 1-16[3)] |
| Type | Propylene-ethylene copolymer | Propylene-ethylene copolymer | Propylene homopolymer | Propylene-ethylene copolymer |

TABLE 1-continued

| Polyolefins used | | | | |
|---|---|---|---|---|
| | Polyolefin 1 | Polyolefin 2 | Polyolefin 3 | Polyolefin 4 |
| Softening point (° C.) | 83[4] | 88 | 145[4] | 106 |
| Viscosity at 170° C. (mPa·s) | 180 | 11500 | 101 | 4300 |
| $M_n$ | 2760 | 8250 | 1980 | 5320 |
| $M_w$ | 6320 | 19110 | 3900 | 12030 |

[1] Polymerization data: total ethylene usage 400 g, polymerization temp. 75° C.
[2] Total ethylene usage 350 g, polymerization temp. 65° C.
[3] Total ethylene usage 200 g, polymerization temp. 50° C.
[4] Dropping point The polyolefins 1 to 4 which are described in detail above were melted together with the additional components shown in Table 2 in the mixing ratios indicated and mixed at a temperature of 170° C.

TABLE 2

Illustrative formulations and comparative formulations (reported in % by weight) and resulting initial peel values in N/mm², measured at 37° C.

| | Example | | | | |
|---|---|---|---|---|---|
| | 1 | 2 | 3 | 4 | 5 |
| Polyolefin 1 | 80 | | | | |
| Polyolefin 2 | | 80 | | | |
| Polyolefin 3 | | | 5 | | |
| Polyolefin 4 | | | 75 | 80 | |
| Affinity GA-1900 | | | | | 60 |
| Escorez 5637 | 20 | 20 | 20 | 20 | 40 |
| Oppanol B11 | | | | | |
| Vestoplast 828 | | | | | |
| Initial peel | — | 364 | 544 | — | 205 |

| | Example | | | | |
|---|---|---|---|---|---|
| | 6 | 7 | 8 | 9 | 10 |
| Comparison I SIS based | 100 | | | | |
| Comparison II SIS based | | 100 | | | |
| Huntsman RT-2730 | | | 100 | | |
| Polyolefin 3 | | | | 70 | 30 |
| Escorez 5400 | | | | | 40 |
| Escorez 5637 | | | | 20 | |
| Oppanol B11 | | | | 10 | |
| Vestoplast 828 | | | | | 30 |
| Initial peel | 192 | 205 | 166 | 473 | 392 |

To determine the peel values of the hot melt adhesives tested, nonwoven material BBA Style 717D (16.9 gsm) was adhesively bonded to a polyethylene film Clopay DH-203 PE by means of each of the hot melt adhesives as per illustrative formulations 1 to 10 at 25° C., with in each case 6.2 g/m² of hot melt adhesive being sprayed onto the nonwoven material and the sprayed nonwoven and the film then being promptly pressed together by means of rollers. The specimens were stored for 24 hours at a temperature of 25° C. under standard conditions and then peeled at a speed of 12 inches/min and a peel angle of 180° at 25° C.

The test results show, by way of the initial peel values, a sometimes very large increase in the adhesive strength of the hot melt adhesives containing the polyolefins used according to the invention, compared to hot melt adhesives of the prior art (see Examples 5, 6, 7 and 8). Consequently, a satisfactory adhesive action can be achieved even when using the hot melt adhesives of the invention in amounts of less than 6 g/m².

Chemical nature of the commercial products used:

| | |
|---|---|
| Affinity GA-1900 | Polyethylene (Dow Chemical Corp.) |
| Escorez 5637 | Hydrocarbon resin (ExxonMobil) |
| Escorez 5400 | Hydrocarbon resin (ExxonMobil) |
| Oppanol B11 | Polyisobutene (BASF) |
| Vestoplast 828 | amorphous poly-alpha-olefin (Degussa) |
| Huntsman RT-2730 | amorphous poly-alpha-olefin (Huntsmann) |
| Comparison I SIS based | hot melt adhesive formulation comprising styrene-isoprene block copolymer, oil, resin (H B Fuller) |
| Comparison II SIS based | hot melt adhesive formulation comprising styrene-isoprene block copolymer, oil, resin (National Starch) |

The invention claimed is:

1. A hot melt adhesive for adhesively bonding fibrous materials to one another or to smooth substrate surfaces, comprising at least one polyolefin prepared by polymerization in the presence of metallocene as catalyst and has a ring/ball softening point in the range from 50 to 165° C. and a melt viscosity measured at a temperature of 170° C. in the range from 100 to 20,000 mPa·s, wherein the at least one polyolefin is a copolymer of propylene with at least one or more further monomers selected from the group consisting of ethylene and linear or branched 1-olefins having from 4 to 20 carbon atoms, with the content of structural units derived from propylene being from 70 to 99.9% by weight and wherein the hot melt adhesive is free of plasticators, plasticizers or both.

2. The hot melt adhesive as claimed in claim 1, wherein the at least one polyolefin has a glass transition temperature $T_g$ of not more than −10° C. and a melt flow index MFI of greater than 30 g/10 min, measured in accordance with ISO 1133 at a temperature of 190° C. and under a load of 2.16 kg.

3. The hot melt adhesive as claimed in claim 1, wherein the hot melt adhesive is water- and solvent-free.

4. The hot melt adhesive as claimed in claim 1, wherein the at least one polyolefin is present in an amount of from 2 to 100% by weight.

5. The hot melt adhesive as claimed in claim 1, further comprising one or more tackifiers selected from the group of resins consisting of aliphatic, cycloaliphatic or aromatic hydrocarbon resins, polyterpene resins prepared by polymerization of terpenes in the presence of Friedel-Crafts catalysts, hydrogenated polyterpenes, copolymers and terpolymers of natural terpenes, styrene-terpene, α-methylstyrene-terpene copolymers, natural resins, modified rosins, resin esters, glyceryl esters of tree resins, pentaerithrityl esters of tree resins, tall oil resins and hydrogenated derivatives thereof, phenol-modified pentaerithrityl esters of resins and phenol-modified terpene resins and amorphous poly-alpha-olefins.

6. The hot melt adhesive as claimed in claim 1, wherein the hot melt adhesive contains at least one of resin in an amount, based on the total weight of the hot melt adhesive, in the range from 0 to 60% by weight and wherein aliphatic, cycloaliphatic or aromatic hydrocarbon resins.

7. The hot melt adhesive as claimed in claim 1, further comprising at least one constituent selected from the group consisting of pigments, antioxidants, odor binders, antimicrobial agents, colorants and fragrances.

8. A method for laminating fiber materials to one another, comprising the step of applying a hot melt adhesive between the fiber materials, wherein the holt melt adhesive comprises at least one polyolefin prepared by polymerization in the presence of metallocene as catalyst and has a ring/ball softening point in the range from 50 to 165° C. and a melt viscosity measured at a temperature of 170° C. in the range from 100 to 20,000 mPa·s, wherein the at least one polyolefin is a copolymer of propylene with at least one or more further monomers selected from the group consisting of ethylene and linear or branched 1-olefins having from 4 to 20 carbon atoms, with the content of structural units derived from propylene being from 70 to 99.9% by weight and wherein the hot melt adhesive is free of plasticators, plasticizers or both.

9. The method as claimed in claim 8, wherein the hot melt adhesive is applied in an amount of from 1 to 6 g/m².

10. The method as claimed in claim 8, wherein fiber material is selected from the group consisting of cotton, wool, silk, cellulose, linen, polyamide, polyester, polyethylene terephthalate, polypropylene terephthalate, polyvinyl chloride, propylene, polyethylene or mixtures thereof.

11. The method as claimed in claim 8, wherein the film is selected from the group consisting of polyethylene terephthalate, polycarbonate, polyethylene, polypropylene, polyvinyl chloride and polystyrene.

12. A hygiene article, a panty diaper, diaper, incontinence product, panty liner or sanitary towel comprising a hot melt adhesive, wherein the holt melt adhesive comprises at least one polyolefin prepared by polymerization in the presence of metallocene as catalyst and has a ring/ball softening point in the range from 50 to 165° C. and a melt viscosity measured at a temperature of 170° C. in the range from 100 to 20,000 mPa·s, wherein the at least one polyolefin is a copolymer of propylene with at least one or more further monomers selected from the group consisting of ethylene and linear or branched 1-olefins having from 4 to 20 carbon atoms, with the content of structural units derived from propylene being from 70 to 99.9% by weight and wherein the hot melt adhesive is free of plasticators, plasticizers or both.

13. The hot melt adhesive as claimed in claim 1, wherein the at least one polyolefin has a melt viscosity measured at a temperature of 170° C. in the range from 100 to 20 000 mPa·s.

14. The hot melt adhesive as claimed in one claim 1, wherein the at least one polyolefin has a number average molar mass $M_n$ in the range from 800 to 10 000 g/mol, and a weight average molar mass $M_w$ in the range from 1600 to 30 000 g/mol.

15. The hot melt adhesive as claimed in one claim 1, wherein the at least one polyolefin has a number average molar mass $M_n$ in the range from 1000 to 5000 g/mol, and a weight average molar mass $M_w$ in the range from 2000 to 20 000 g/mol.

16. The hot melt adhesive as claimed in claim 1, wherein the linear or branched 1-olefins having from 4 to 10 carbon atoms.

17. The hot melt adhesive as claimed in claim 1, wherein the content of structural units derived from propylene being from 80 to 99% by weight.

18. The hot melt adhesive as claimed in claim 1, wherein the at least one polyolefin is present in an amount of from 30 to 95% by weight.

19. The hot melt adhesive as claimed in claim 1, wherein the at least one polyolefin is present in an amount of from 50 to 85% by weight.

20. The hot melt adhesive as claimed in claim 1, wherein the at least one polyolefin is present in an amount of from 70 to 80% by weight.

21. The hot melt adhesive as claimed in claim 1, wherein the hot melt adhesive contains at least one of resin in an amount, based on the total weight of the hot melt adhesive, in the range from 10 to 50% by weight.

22. The hot melt adhesive as claimed in claim 1, wherein the hot melt adhesive contains at least one of resin in an amount, based on the total weight of the hot melt adhesive, in the range from 15 to 30% by weight.

23. A diaper, panty diaper, incontinence product, panty liner or sanitary towel produced with a hot melt adhesive, wherein the holt melt adhesive comprises at least one polyolefin prepared by polymerization in the presence of metallocene as catalyst and has a ring/ball softening point in the range from 50 to 165° C. and a melt viscosity measured at a temperature of 170° C. in the range from 100 to 20,000 mPa·s, wherein the at least one polyolefin is a copolymer of propylene with at least one or more further monomers selected from the group consisting of ethylene and linear or branched 1-olefins having from 4 to 20 carbon atoms, with the content of structural units derived from propylene being from 70 to 99.9% by weight and wherein the hot melt adhesive is free of plasticators, plasticizers or both.

24. The method as claimed in claim 8, wherein the hot melt adhesive is applied in an amount of from 3 to 5.5 g/m2.

* * * * *